(12) United States Patent
Deyerling et al.

(10) Patent No.: US 7,812,210 B2
(45) Date of Patent: Oct. 12, 2010

(54) REFUSE TREATMENT PLANT

(75) Inventors: Lothar Deyerling, Reichersbeuren (DE);
Ambros Bauer, Warngau (DE)

(73) Assignee: W. L. Gore & Associates, GmbH, Putzbrunn (DE)

( * ) Notice: Subject to any disclaimer, the term of this patent is extended or adjusted under 35 U.S.C. 154(b) by 672 days.

(21) Appl. No.: 11/568,816

(22) PCT Filed: May 25, 2005

(86) PCT No.: PCT/EP2005/005648

§ 371 (c)(1),
(2), (4) Date: Oct. 9, 2007

(87) PCT Pub. No.: WO2005/115646

PCT Pub. Date: Dec. 8, 2005

(65) Prior Publication Data

US 2008/0051620 A1    Feb. 28, 2008

(30) Foreign Application Priority Data

May 28, 2004   (DE) ................ 10 2004 026 694

(51) Int. Cl.
   *C21B 3/06* (2006.01)
(52) U.S. Cl. ................. 588/251; 588/259; 588/900
(58) Field of Classification Search ............ 588/251, 588/259, 900
   See application file for complete search history.

(56) References Cited

U.S. PATENT DOCUMENTS

| | | | |
|---|---|---|---|
| 3,895,916 A | 7/1975 | Rosner | 23/259.1 |
| 3,953,566 A | 4/1976 | Gore | 264/288 |
| 4,187,390 A | 2/1980 | Gore | 174/102 R |

FOREIGN PATENT DOCUMENTS

| | | |
|---|---|---|
| DE | 42 31 414 | 3/1994 |
| WO | WO01/21394 | 3/2001 |
| WO | WO/2004/048719 | 6/2004 |

*Primary Examiner*—Edward M Johnson
(74) *Attorney, Agent, or Firm*—Bridget C. Sciamanna

(57) ABSTRACT

The invention relates to a refuse treatment plant (1) with a closed construction, which permits the aerobic degradation of organic material, for example in refuse comprising biodegradable fractions. The refuse treatment plant (1) comprises a bay (5) with an aeration and deaeration installation. At least one refuse treatment chamber (16), which is connected to the bay (5) via an opening (7) in the bay wall, is located on at least one external face of the bay wall (6). The refuse treatment chamber (16) is configured by a cover tarpaulin (30), which is provided with a raising and lowering device (20), is water-and particle-tight but permeable to air and water vapour. The cover tarpaulin (30) comprises an edge (32), which is attached to the bay wall (6) and to the ground (50) in a rigid and airtight manner by means of a fixing device (50). The raising and lowering device (20) can be configured with the aid of a pneumatic support structure (22) consisting of inflatable tubes (23). The cover tarpaulin (30) is raised for the respective charging and discharging process of the refuse treatment chamber (16), so that refuse can be transported into or out of the bay (5) through the opening (7) in the bay wall. The raising and lowering device (20) is lowered for the duration of the aerobic treatment process, in such a way that the cover tarpaulin (30) lies directly on the refuse to be treated.

27 Claims, 13 Drawing Sheets

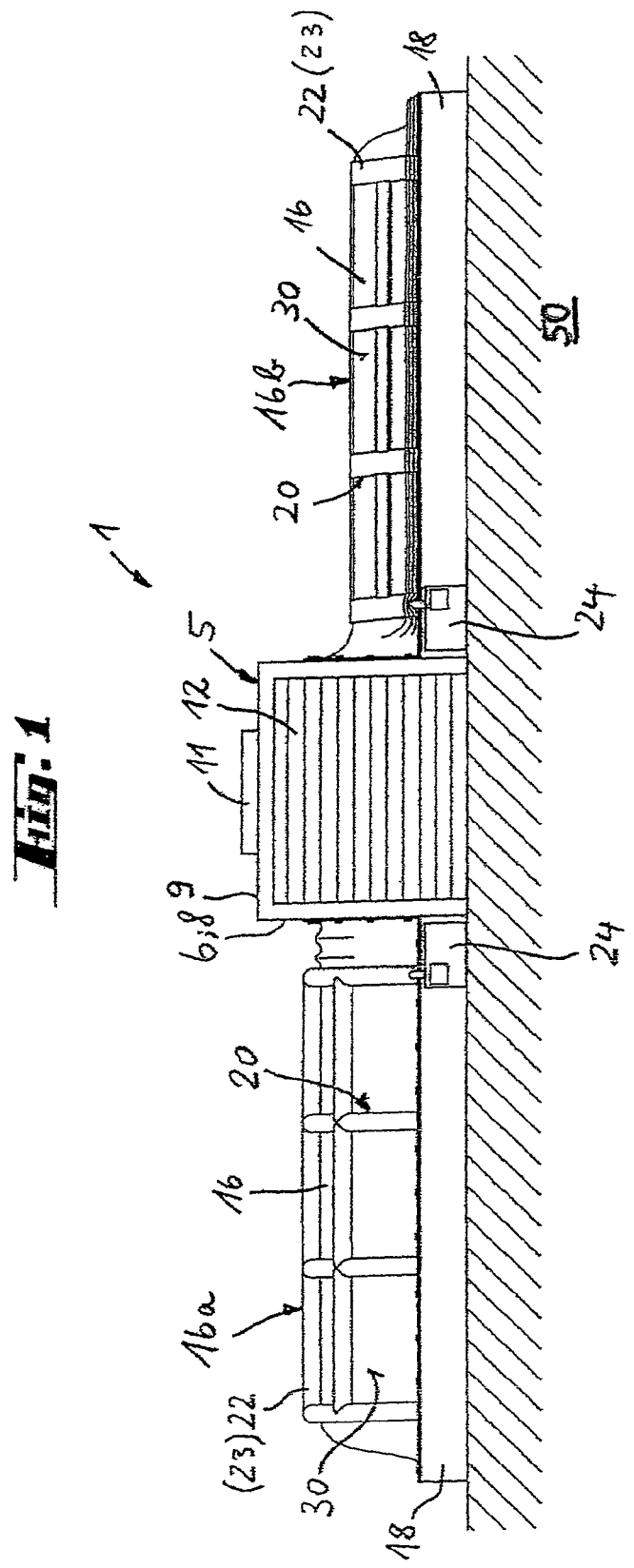

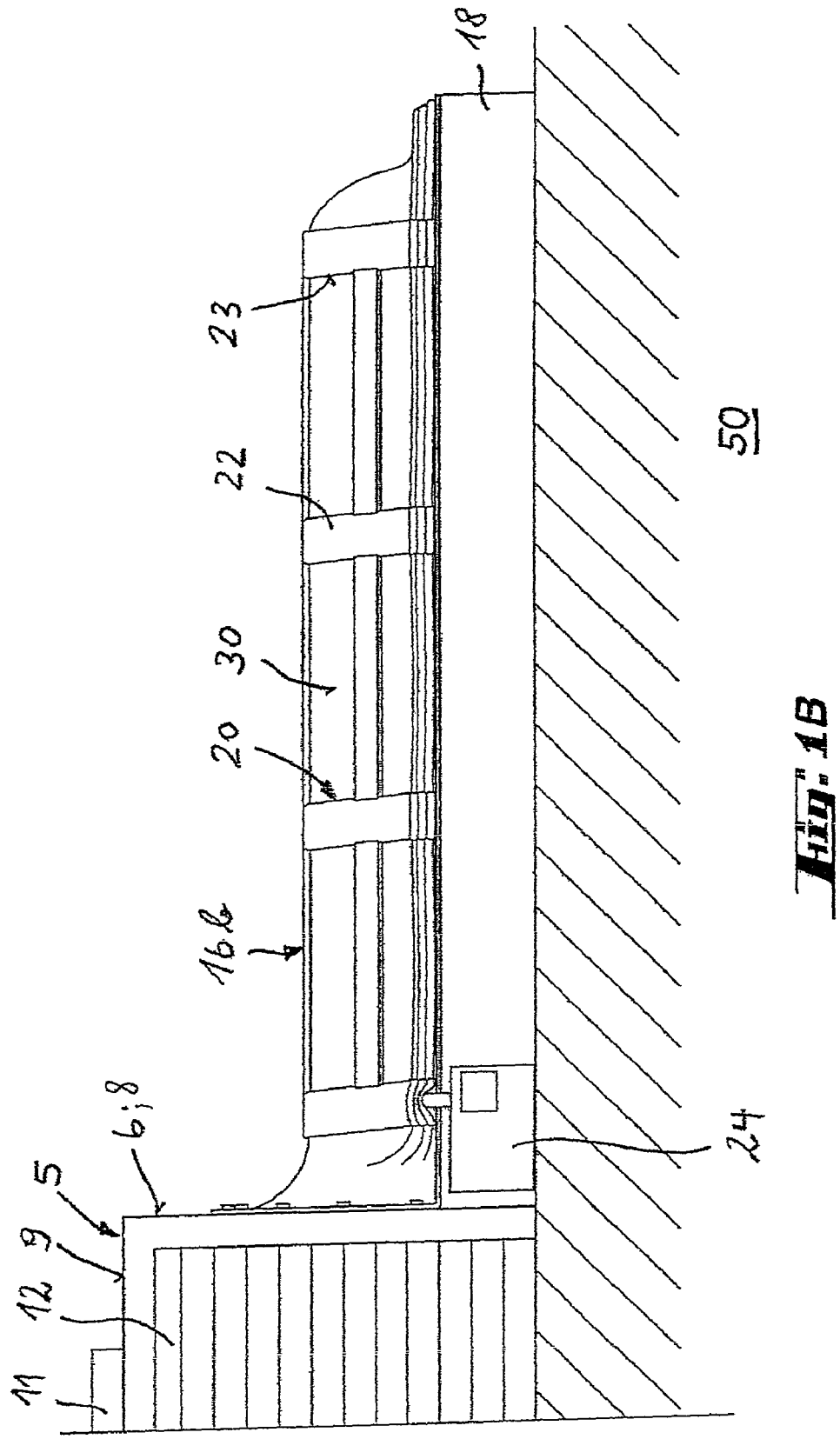

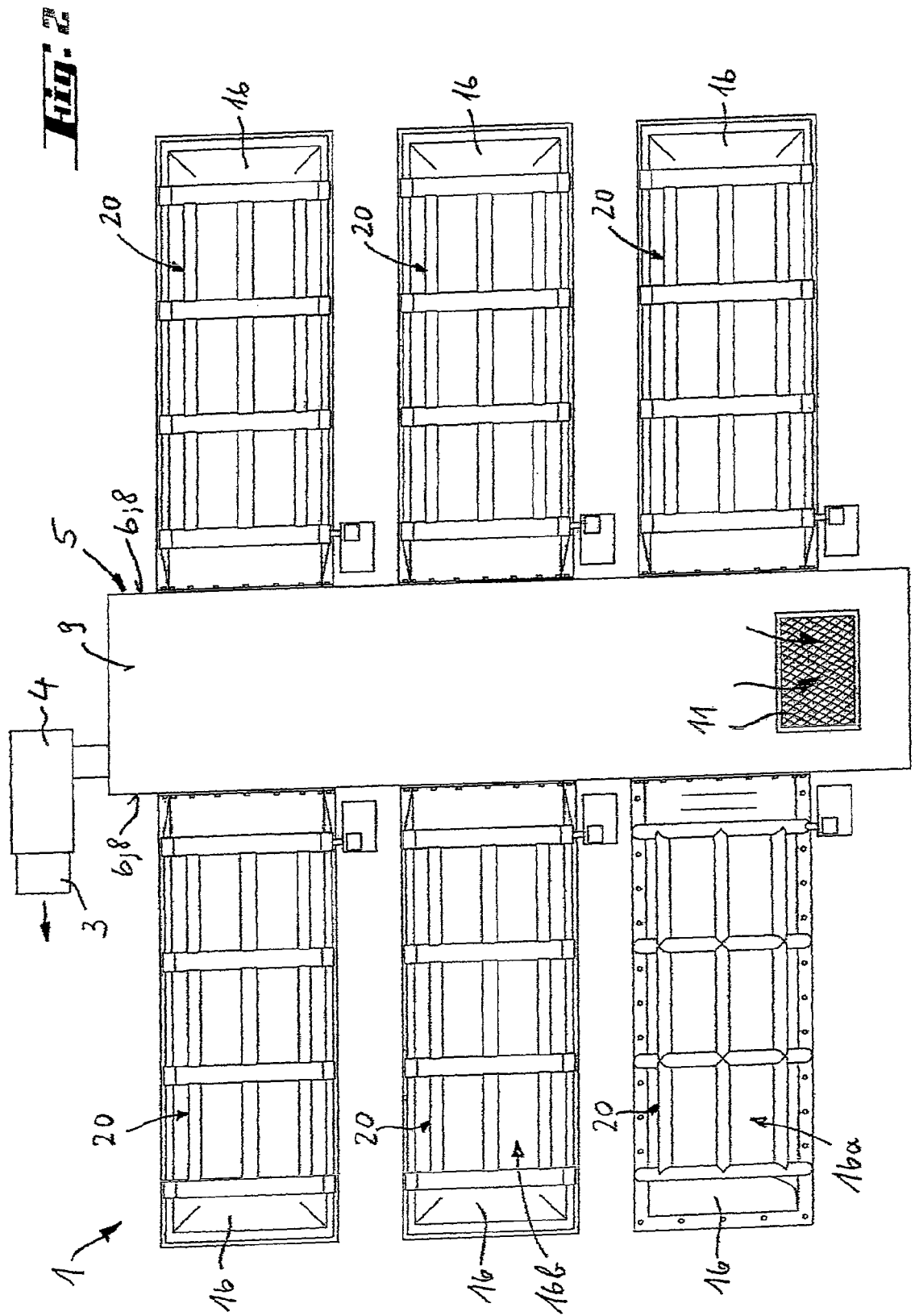

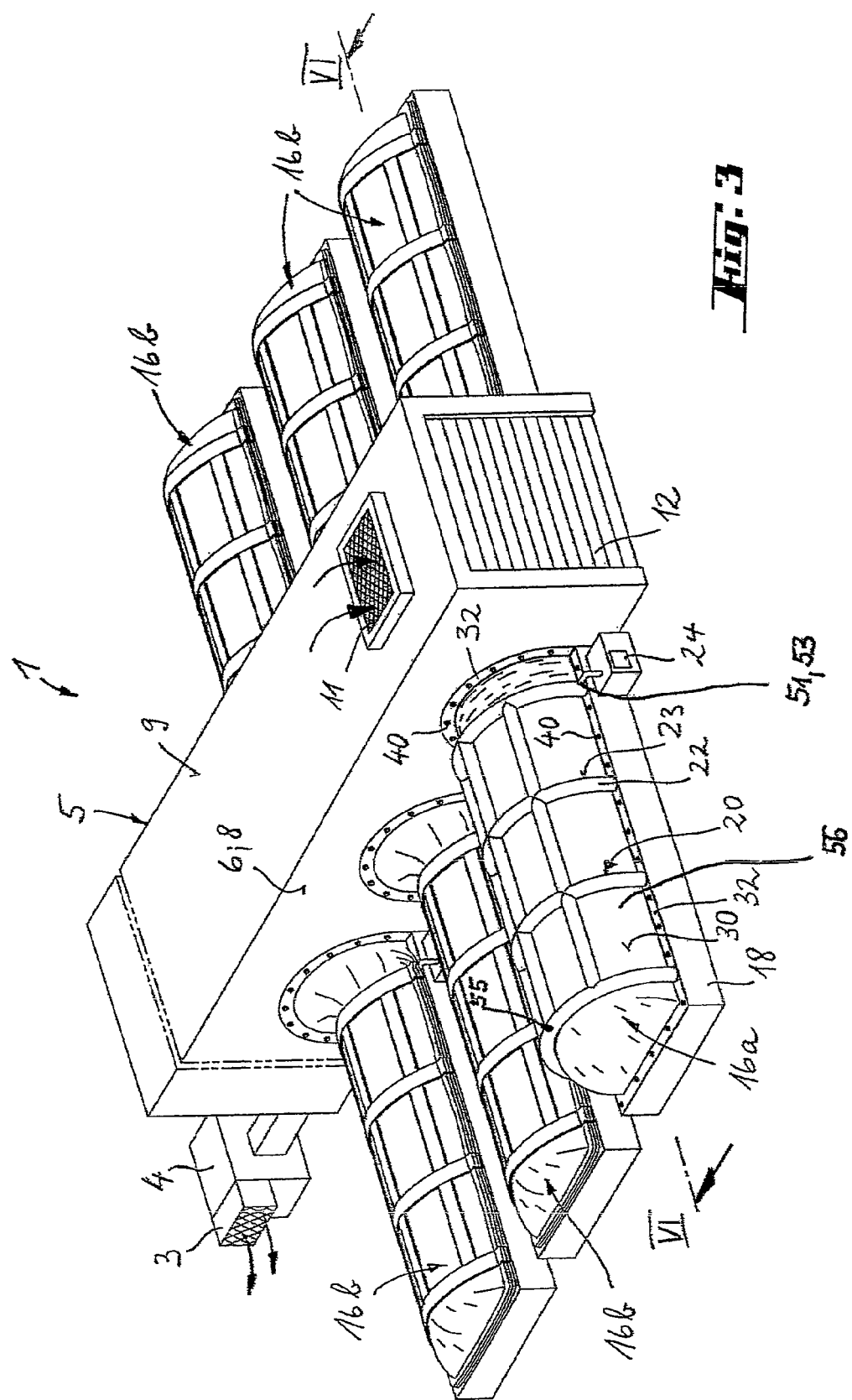

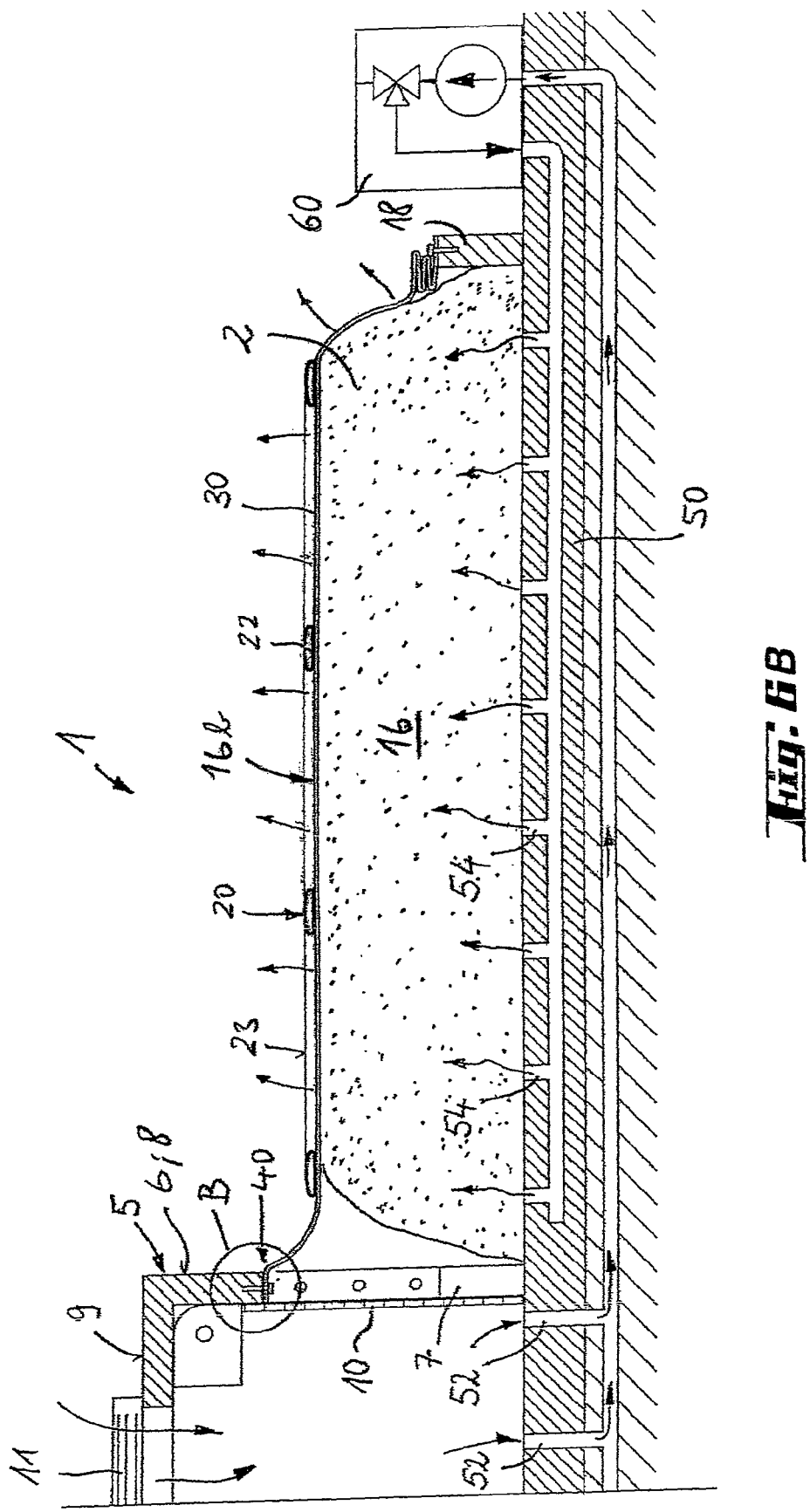

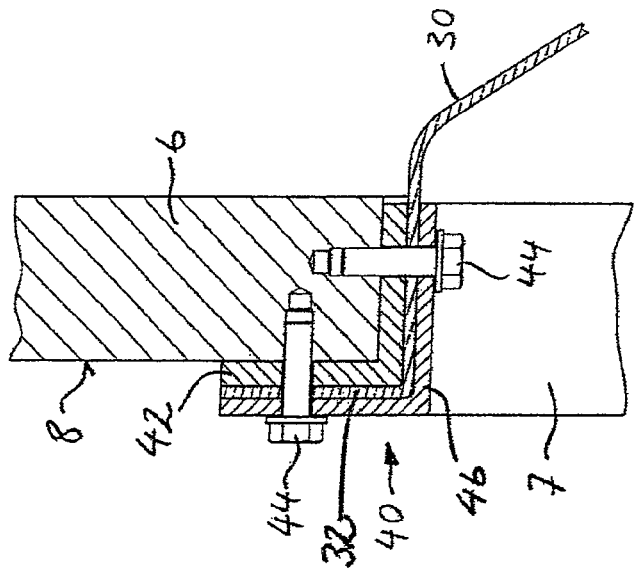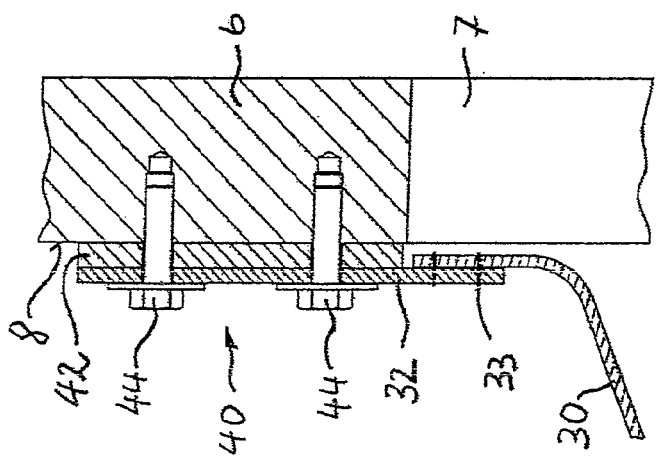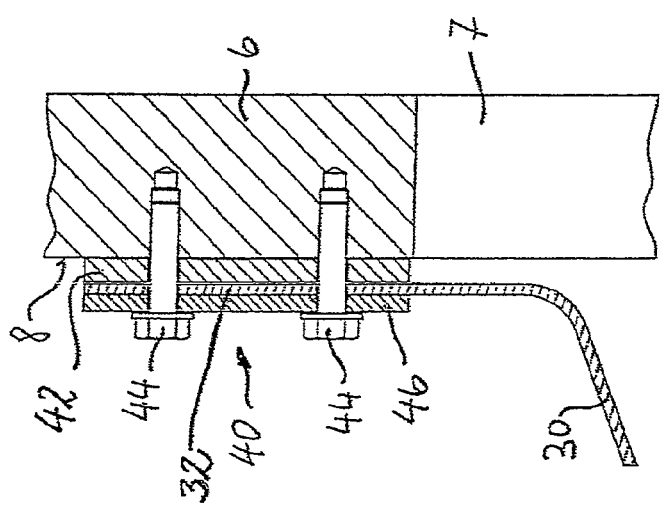

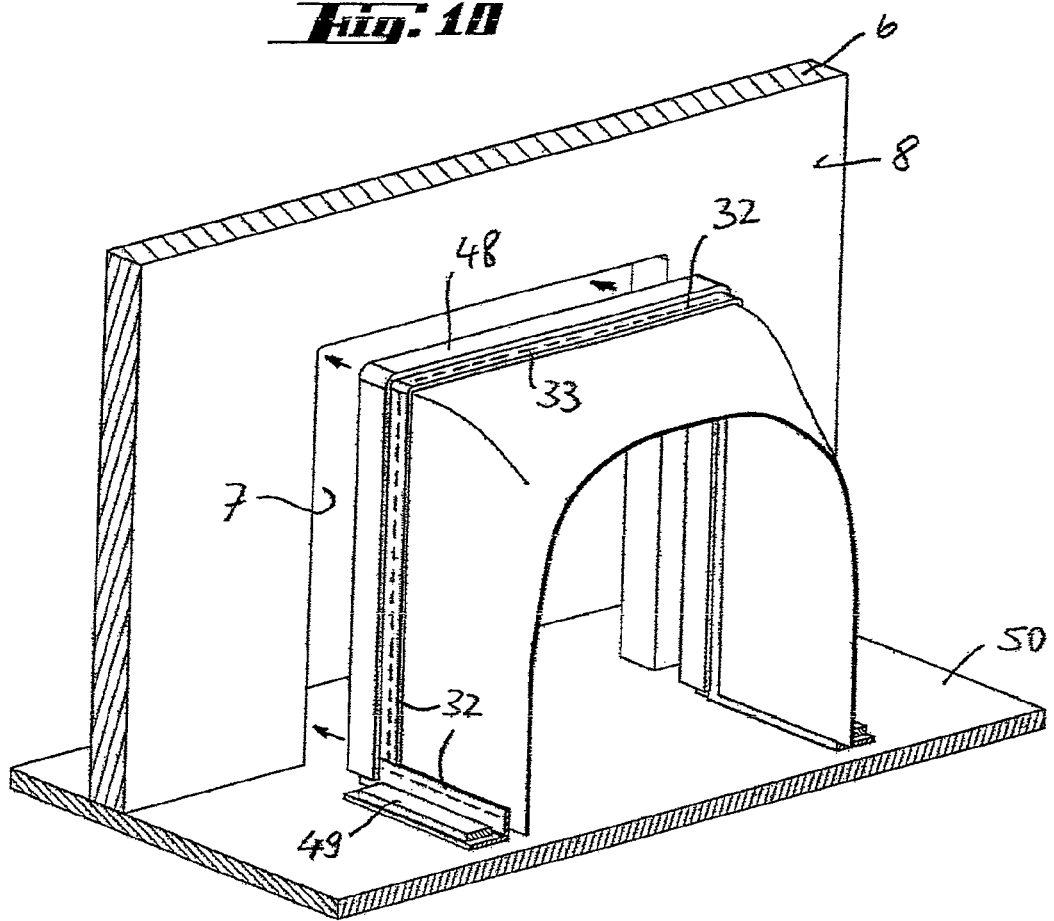

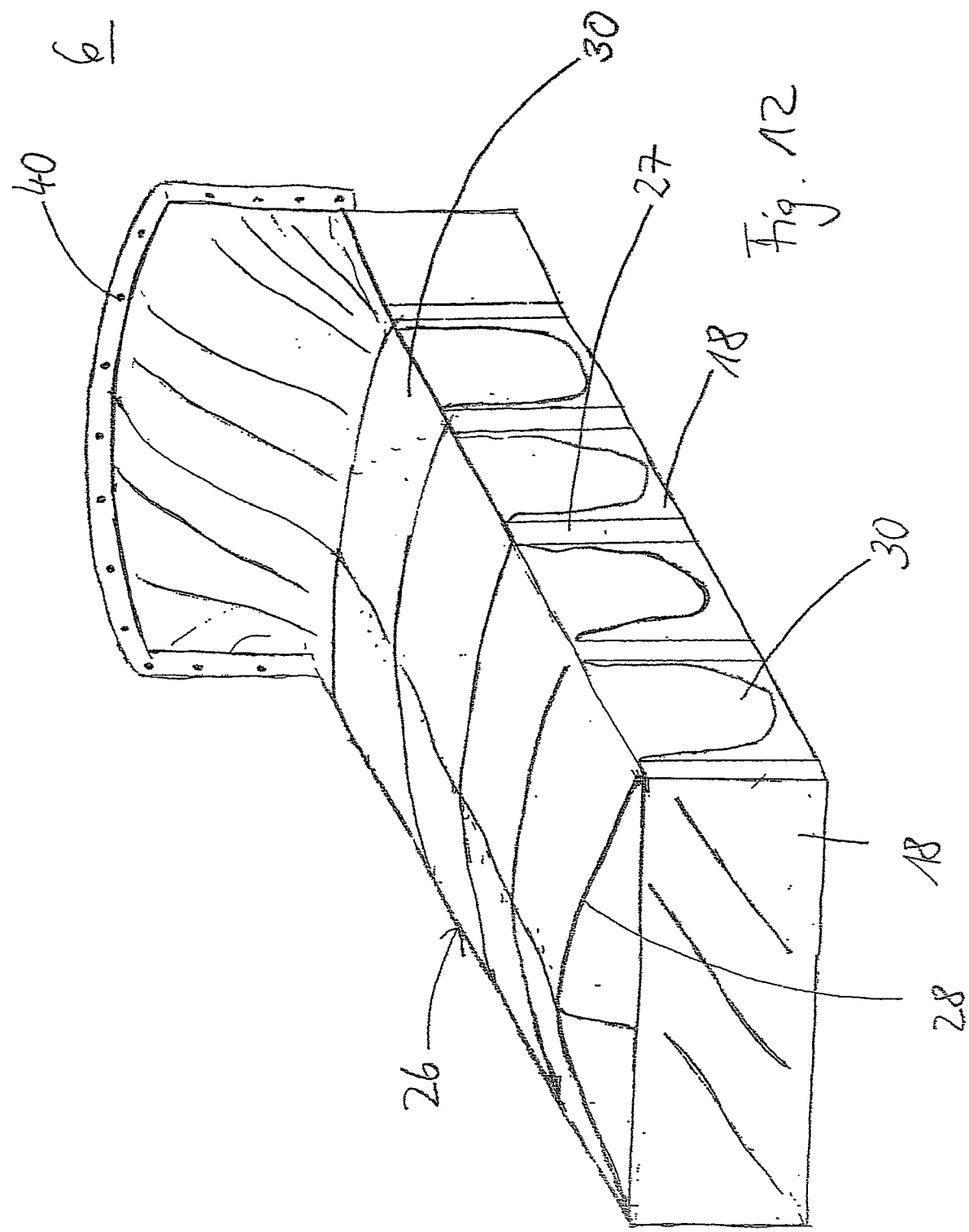

REFUSE TREATMENT PLANT

The present invention relates to the biological aerobic degradation of organic material, for example in refuse comprising biodegradable fractions. The invention relates, in particular, to a refuse treatment plant of closed type of construction, with a watertight and particle-tight covering tarpaulin which, however, is permeable to air and to water vapor.

In the field of refuse treatment, various devices and methods for the drying and aerobic degradation of biological constituents of solid housing refuse are known. A problem which has existed for a long time in aerobic refuse treatment is the waste air which in this case occurs and has a high fraction of harmful emissions, such as aerosols, dust, germs, VOCs (volatile organic compounds) and odorous substances, which may be detrimental to health and are subject to regional limit value emissions. In many simple plants for refuse treatment, there are problems with the control of germ emissions and odors, since all the gases which arise can escape, unimpeded, into the surrounding atmosphere.

To eliminate these problems, for some years, aerobic refuse treatment has been carried out in closed systems and involves composting in structurally closed buildings, and also in containers, rotting tunnels or boxes. Closed systems of this type are deemed to be airtight, since the waste air remains in the building and is suction-extracted from there in a controlled way. Disadvantages of this closed system are the high investment costs in the procurement of such a device and also the high costs incurred in discharging and purifying the waste air arising within the system. In particular, the costs for waste air treatment with biofilters or bioscrubbers are very high.

Alternatively to the closed plants, for some years, large-area permeable covering tarpaulins have been used, which completely cover piled-up refuse heaps. The permeability of these coverings is selected such that the refuse heap can be actively aerated and, at the same time, protection against germ emission and also odor reduction are afforded. For example, DE 4231414 C2 describes a covering for a compost heap, with a watertight and gas-permeable membrane laminate. However, such coverings have various disadvantages. On the one hand, the dumping and covering of the refuse heaps take place one after the other in time, that is to say the heap first has to be dumped partially or completely before the covering tarpaulin can be pulled over it. As long as air flows freely over the open uncovered heap, this leads to undesirable emissions. Moreover, to demolish the heap, the covering has to be removed from the heap, so that the demolition appliances have free access to the refuse heap and do not cause any damage to the covering. The removal of the covering leads, once again, to undesirable emissions. The delivered refuse often has to undergo pretreatment, such as sorting, communition or mixing. After this pretreatment, the waste is transported, open, across country as far as the heap and during this time likewise discharges undesirable emissions into the surroundings.

On the other hand, the complicated and at least partially manual handling involved in laying down and removing the covering tarpaulin entails considerable labor in terms of personnel. The handling of the covering is made even more difficult by the high piling height of the heap. Furthermore, marginal weighting equipment for holding down the covering tarpaulin, such as, for example, water-filled fire hoses and sand bags, have to be removed and put in place again later. The use of mechanical winding machines for applying and pulling off the covering tarpaulins also advantageously require at least two persons. Furthermore, damage to the tarpaulin material may occur due to the covering tarpaulin being rolled up and unrolled, thus greatly reducing the functionality of the covering tarpaulin, particularly in the case of a membrane material. Even in terms of work safety, working with covering tarpaulins on refuse heaps is not without problems for the responsible personnel. On the one hand, there is the risk of accidents in stepping on and walking over the heap. On the other hand, if a heap is not covered, the personnel is in direct contact with the material to be covered and with the emerging emissions, thus constituting a risk to the health of the personnel. In a further development, the covering tarpaulins are provided with inflatable supporting elements which can raise and lower the covering tarpaulin for the purpose of building up and breaking down the rotting heap, without the covering tarpaulin having to be removed from the heap. Here, too, however, there is still the problem of the emerging emissions, since, while the rotting heap is being built up and broken down, there must be free access to the heap and in this time harmful emissions may pass, unimpeded, into the surrounding air.

There are noticeable tendencies for legislation and also national and regional licensing authorities to give preference to closed systems in future.

The object of the present invention, therefore, is to provide an improved and more cost-effective refuse treatment plant for the aerobic degradation of organic constituents in refuse, which at the same time constitutes a system closed with respect to the surroundings.

The object of the present invention is, furthermore, to provide a refuse treatment plant, using heap coverings which avoid harmful emissions into the surroundings even when the heap is being built up and broken down.

The object is achieved, according to the invention, by means of the features of claim 1. The dependent claims specify advantageous refinements of the invention.

The object is achieved by means of a refuse treatment plant with a bay with at least one bay wall, with a bay roof and with an access for the introduction and removal of refuse, with an aeration and deaeration plant for the supply and discharge of air into and out of the bay, and with at least one refuse treatment space, arranged on an outside of the bay wall, for the aerobic degradation of the organic constituents in the refuse. The bay is connected to the refuse treatment space via a bay wall aperture which serves for introducing the refuse from the bay into the refuse treatment space and for removing the treated refuse from the refuse treatment space into the bay. The refuse treatment space is formed by a covering tarpaulin provided with a raising and lowering device. The covering tarpaulin has a covering tarpaulin margin which is arranged rigidly, and so as to be airtight, with respect to the bay wall and to the floor by means of a fastening device.

The refuse treatment plant according to the invention forms a closed system and links a closed bay to a heap covering to form a unitary system. In particular, by means of such a plant, it is possible to keep the refuse in spaces closed with respect to the surroundings from delivery, through its pretreatment and subsequent aerobic treatment, up to discharge, so that a contact of harmful emissions with the surrounding air is as far as possible avoided.

By means of the plant, the aerobic treatment is shifted out of the bay into the adjoining refuse treatment spaces. The bay wall aperture is closeable, for example a door or a gate separates the refuse treatment space in an airtight manner from the interior of the bay. The bay wall aperture is opened solely for filling or emptying the refuse treatment space, the bay wall aperture remaining closed for the entire duration of treatment.

The bay can consequently have a substantially smaller dimensioning and build. The bay is required only for receiving the refuse and for processing work, necessary where appropriate, such as, for example, communition or mixing. The investment costs for the entire plant consequently fall, especially since a lower aeration and deaeration capacity is required due to a smaller bay. In conjunction with this, smaller and therefore more cost-effective bay deaeration systems may be provided. A following biofilter may likewise have smaller dimensioning. Since the quantity of waste air to be treated is far smaller than in the closed plants in the prior art, the investment and operating costs of the plant according to the invention are reduced. Moreover, the bay has a substantially longer lifetime, since it is no longer used for the intensive aerobic treatment processes.

In one embodiment, the covering tarpaulin has a watertight and gas-permeable membrane. The membrane acts as a protective barrier inwardly and outwardly. Inwardly, the membrane protects against the ingress of water and against drying out under strong solar radiation. Outwardly, the membrane protects against germ emissions and the emergence of odors and, on account of its gas-permeability, has the effect that the $CO_2$ and air occurring in the refuse treatment space due to aerobic degradation can escape through the membrane, without a pressure build-up occurring on the covering tarpaulin. The waste air from the refuse treatment spaces does not have to be specially suction-extracted, since this escapes, prepurified, through the gas-permeable membrane into the surroundings. The pore structure of the membrane causes all the harmful constituents to be filtered out from the waste air. Preferably, the watertight and gas-permeable membrane is porous. Owing to the porous configuration of the membrane, the covering tarpaulin has an air-permeability of between 3 and 100 $m^3/m^2/h$ in the case of a pressure difference of 200 Pa.

Moreover, the covering tarpaulin together with a membrane has a water vapor flow resistance of less than 20 $m^2$ Pa/W and consequently ensures a high water vapor flow through the covering tarpaulin. This low water vapor flow resistance makes it possible to dry wet material or to transport away process water which occurs. Lumping and watering of the refuse and putrefaction processes associated with this are prevented. The water vapor flow and the air-permeability ensure that the refuse to be treated is sufficiently aerated, that is to say supplied with sufficient oxygen, and reaction products can escape without a pressure build-up. Furthermore, the covering tarpaulin together with the membrane is leak-tight with respect to water in the case of a water inlet pressure of higher than 10 kPa. This ensures protection against wetting through by rainwater.

Preferably, the membrane is connected to at least one textile layer. The use of a textile laminate is particularly advantageous, since, in addition to the high watertightness and simultaneous gas-permeability, the porous membrane is particularly suitable for the simultaneous retention of emissions, such as odors and germs.

The covering tarpaulin of the refuse treatment space is provided with a raising and lowering device in order to adjust the height of the covering tarpaulin. Height adjustment is necessary for filling or emptying the treatment space by means of wheeled loaders or telescopic conveyor belts, pusher floors or scraper floors or similar technologies. This means that, for loading or emptying the refuse treatment space, the covering tarpaulin must be at a sufficiently long distance from the refuse, so that the appliances or machines can move into the refuse treatment space.

During the aerobic treatment process, it is advantageous if the covering tarpaulin lies directly on the refuse to be treated. As a result, the aerobic degradation processes are accelerated, and the water vapor flow through the covering tarpaulin is promoted. For this reason, during aerobic treatment, the covering tarpaulin is lowered and lies directly on the refuse. The raising and lowering of the covering tarpaulin take place with the exception of the covering tarpaulin margin. So that the refuse treatment space remains a closed system during the raising and lowering of the covering tarpaulin, the covering tarpaulin margin is arranged rigidly and so as to be airtight with respect to the bay and to the floor by means of a fastening device. The fastening device fixes the covering tarpaulin margin in the front region of the refuse treatment space to the outside of the bay wall. The covering tarpaulin margin in the side regions and the end region of the refuse treatment space is fixed either directly to the floor or to/on the add-on walls by means of a fastening device. In this context, the term "airtight" means that no waste air should escape toward the floor from inside the plant via the connection between the bay and treatment space, including the fastening. A rigid fastening means that the covering tarpaulin margin is fastened immovably to the bay wall and the floor or to/on the add-on walls. The covering tarpaulin moves during the raising and lowering operations, but not the covering tarpaulin margin.

In one embodiment, a pneumatic raising and lowering device is provided, the pneumatic raising and lowering device providing a number of inflatable hoses. The raised state of the device is implemented by the hoses which are filled with air under pressure. The covering tarpaulin is thereby raised and forms a drive-in bay or a space in which the refuse to be treated can be piled up or stacked.

In the lowered state of the device, the hoses contain essentially no air, that is to say the hoses are empty and the covering tarpaulin covers the refuse heap. The covering tarpaulin thus rests on the refuse in the same way as a conventional heap covering.

In a further embodiment, the hoses are filled with a liquid. The fastening device comprises fixing elements, such as, for example, screws, clamps, nails, rivets or tension devices, the anchoring of the fixing elements in the bay wall and in the floor or in the add-on wall taking place over a large area and sealingly.

In particular, the refuse treatment space is designed to be particle-tight with respect to the surroundings.

Advantageously, the fastening device has an adaptable material. This adaptable material is arranged between the covering tarpaulin margin and the bay wall and also between the covering tarpaulin margin and the floor or the add-on walls. The material has the function of compensating unevennesses in the walls and in the floor, so that no unwanted air penetrates via air ducts or air bridges in the walls and in the floor out of the interior of the plant into the surroundings. The unwanted-air rate of the entire plant is thus lowered. Any flexible material which is easily deformable may be used as adaptable material. For example, elastic plastics, such as foams or rubbers, textile materials, such as woven or knitted fabrics or nonwovens, preferably with a watertight coating or hydrophobic finish, may be employed. The adaptable material may be used in sheet form as strips or a band, and even sealing cords may be employed, as long as there is sufficient material to fill, in an airtight manner, possible ducts, grooves, scores, orifices and other bulges. Depending on the size and depth of the orifices to be sealed off, the material should be introduced in a single ply or in a plurality of plies.

In one embodiment, a clamping frame is provided, into which the covering tarpaulin margin is clamped so as to be airtight. The clamping frame itself is clamped, airtight, into a bay wall aperture or is fastened in any other known way, and is fastened correspondingly to the floor or to/on the add-on walls.

Further advantages and features of the invention are illustrated in the following description of the drawings and particular embodiments.

Definitions and Test Methods:

Aeration and deaeration plant: (Waste gas purification) device for reducing the emission of emission-relevant air impurities in the waste gas of the biological refuse treatment plant, in particular for limiting the emissions of odorous substances, climate-relevant gases, organic substances and dusts and for the reduction of viable and multipliable microorganisms.

Refuse treatment plant: Refuse treatment plant, in which housing refuse or other refuse having biologically degradable fractions is treated by means of biological or a combination of biological and physical methods. These include, in particular, devices for the biological treatment of the refuse under aerobic conditions.

Emissions are the air impurities emanating from a biological refuse treatment plant. The waste gas streams of a refuse treatment plant must adhere to specific emission limit values which are laid down, for example for Germany, in the Federal Emission Protection Law (TA-air) of 24th Jul. 2002.

The term "emissions" is to be understood as meaning in summary the emergence of dusts, aerosols, odors, germs, fungal spores, seeds or other similar emissions.

Water Inlet Pressure Test

The water inlet pressure test is a hydrostatic resistance test which is based essentially on pressing water against one side of a material sample and observing the other side of the material sample for the passage of water.

The water pressure is measured according to a test method in which distilled water at 20±2° C. on a material sample having an area of 100 cm$^2$ is increasingly put under pressure. The water rise pressure amounts to 60±3 cm H$_2$O/min. The water pressure is then the pressure at which water appears on the other side of the sample. The exact procedure is regulated in ISO standard No. 811 of 1981. The term "watertight" is to be understood as meaning that a material withstands a water inlet pressure of at least 10 kPa.

The term "porous" is to be understood as meaning a material which has very small microscopic pores through the inner structure of the material and the pores form an interconnected continuous connection or path from one surface of the material to its other surface. According to the dimensions of the pores, therefore, the material is permeable to air and water vapor, but liquid water cannot pass through the pores.

The measurement of the pore size may take place by means of a Coulter Porometer™ produced by Coulter Electronics, Inc., Hialeah, Fla. The Coulter Porometer is an instrument which determines an automatic measurement of the pore size distribution in porous media according to the method described in ASTM Standard E1298-89.

The pore size nevertheless cannot be determined for all available porous materials by means of the Coulter Porometer. In such a case, the pore size may also be determined, using a microscope, such as, for example, a light-optical or electron microscope.

If a microporous membrane is used, this has an average pore size of between 0.1 and 100 μm, the average pore size preferably lying between 0.2 and 10 μm.

Water Vapor Flow Resistance Ret

The Ret value is a specific material property of sheetlike structures or of assembled materials, which determines the latent heat evaporation flow in the case of a uniform partial pressure gradient through a predetermined surface.

The term "water vapor permeable" defines a material which has a water vapor flow resistance Ret of below 150 (m$^2$×Pa)/W. Preferably, the sheetlike structure has a Ret of below 20 (m$^2$×Pa)/W. Water vapor permeability is measured by means of the Hohenstein MDM Dry method which is described in standard test specification No. BPI 1.4 (1987) of the Bekleidungsphysiologischen Instituts e.V. Hohenstein.

Air-Permeability

The air-permeability is given in m$^3$/h per m$^2$ of sheetlike structure and is determined, using an air-permeability tester of Textest Instruments (FX 3300), Zurich. The air-permeability is determined with reference to ISO 9237 (1995).

The term "air-permeable" designates a material which has an air-permeability of between 3 and 100 m$^3$/m$^2$/h in the case of an applied pressure difference of 200 Pa.

Airtight: Means, within the scope of this invention, that no air passes from the inside outward at the connection point of the covering tarpaulin margin and bay wall or the covering tarpaulin margin and floor or add-on walls. This may be checked, when the plant is in operation, by the application of a slight excess pressure. An airtight plant exhibits no mist or vapor plumes at the points to be checked. A check with artificial mist is, of course, also possible.

Within the scope of this invention, airtight also includes particle-tight.

Covering tarpaulin margin: Is the marginal boundary of the covering tarpaulin and runs around the entire covering tarpaulin.

Particle-tight: The refuse treatment space is designated as being particle-tight insofar as it allows a separation of particles >0.3 μm. The term "particles" is to be understood as meaning airborne particles of solid or liquid form, such as, for example, dusts, spores, pollen or aerosols.

The invention will now be explained in more detail with reference to drawings:

FIG. 1 shows a diagrammatic illustration of the refuse treatment plant according to the invention.

FIG. 1B shows a diagrammatic enlargement of the refuse treatment space 16b from FIG. 1.

FIG. 2 shows a diagrammatic top view of the refuse treatment plant according to the invention.

FIG. 3 shows a perspective view of the refuse treatment plant.

FIG. 6B shows a diagrammatic enlargement of the refuse treatment space 16b from FIG. 6.

FIG. 7 shows an enlarged illustration of an embodiment of the fastening device in the region A of FIG. 6.

FIG. 8 shows an enlarged illustration of a further embodiment of the fastening device in the region A in FIG. 6.

FIG. 9 shows an enlarged illustration of a further embodiment of the fastening device in the region B in FIG. 6.

FIG. 10 shows a further embodiment of the fastening device.

FIGS. 11 and 12 show a refuse treatment plant with a treatment space having a mechanical height adjustment structure.

Figure 1A:
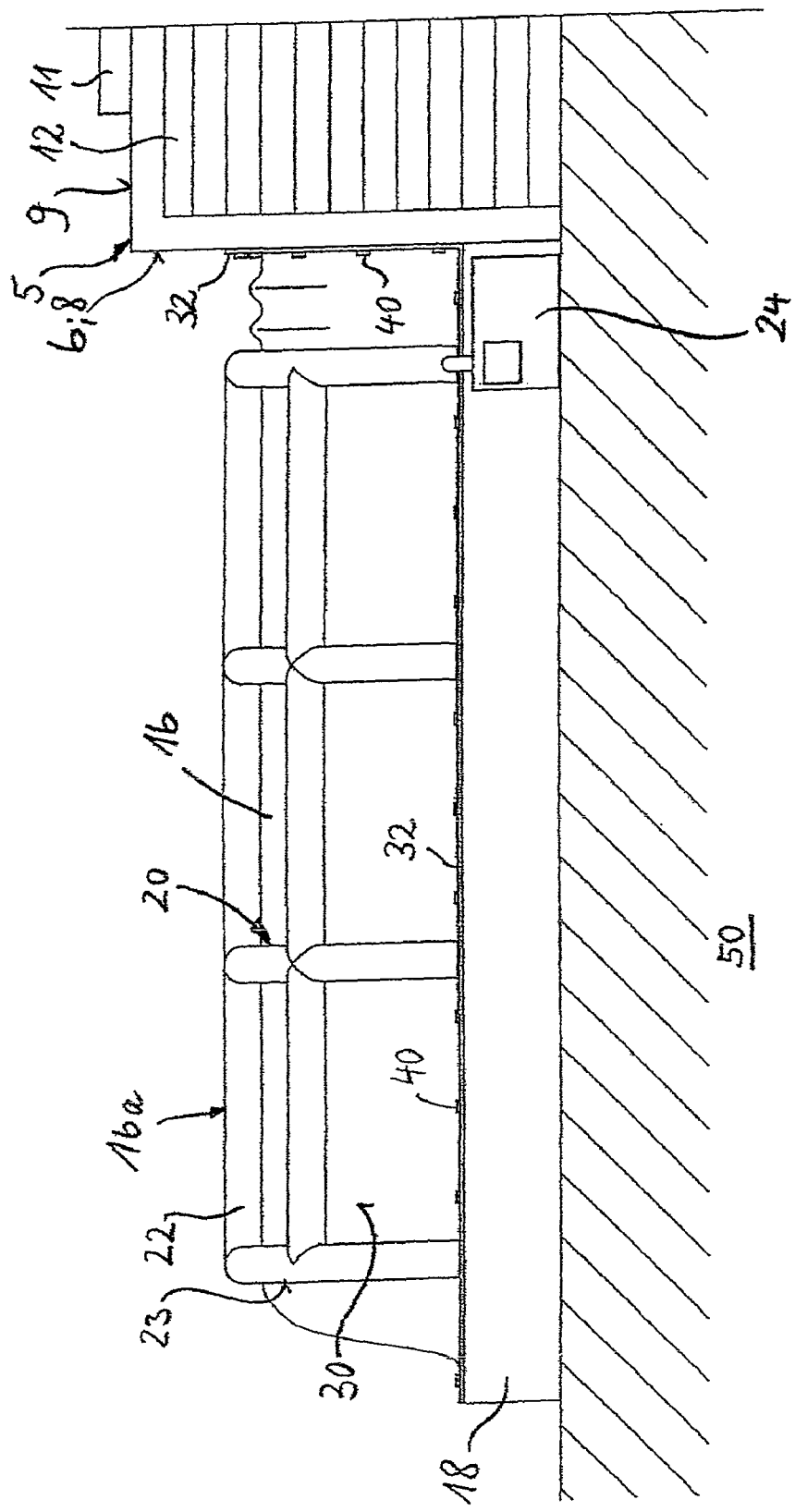
FIG. 1A shows a diagrammatic enlargement of the refuse treatment space 16a from FIG. 1.

FIG. 1 shows a front view of a refuse treatment plant (1) according to this invention. The refuse treatment plant (1) consists of a bay (5) with at least one bay wall (6), with a bay roof (9) and with an access (12). A number of refuse treatment spaces (16) are arranged in each case on the outside (8) of the lateral bay walls (6). An aperture (11), through which air passes into the interior of the bay (5), is arranged in the bay roof (9). The access (12) is the connection between the surroundings and the refuse treatment plant (1) and is preferably arranged closeably in an end-face bay wall (6). The refuse (2) is introduced into and removed from the refuse treatment plant (1) through the access (12). For example, the access (12) is implemented by means of a rolling gate or automatically opening and closing doors.

The bay (5) serves for the reception, pretreatment and distribution of the refuse (2) to be treated, before the latter is subjected in the refuse treatment spaces (16) to the actual aerobic degradation processes. If appropriate, the refuse (2) is comminuted, mixed and/or sorted in the bay (5). The refuse (2) is subsequently built up in at least one refuse treatment space (16) into a refuse heap. In each refuse treatment space (16), the aerobic degradation of the organic constituents of the refuse (2) piled up in layers in it takes place. After the aerobic treatment process, the treated refuse is transported again into the bay (5) and through the access (12) out of the bay (5).

It is also possible to arrange only one refuse treatment space (16) against the bay wall (6). In one embodiment, overall, six refuse treatment spaces are provided, three next to one another in each case. There may be any number of refuse treatment spaces (16), this depending on the size and throughput of the refuse treatment plant (1).

Between the bay (5) and refuse treatment space (16), a lock in the form of a closeable aperture (not illustrated) is provided in the bay wall (6) and connects the interior of the bay (5) to the interior of the refuse treatment space (16). This bay wall aperture serves for introducing the refuse (2) from the bay (5) into the refuse treatment space (16) and for removing the degraded refuse from the refuse treatment space (16) into the bay (5) and should be sufficiently large to ensure that loading and unloading vehicles or appliances, such as wheeled loaders, roller floors or conveyor belts, can pass through the aperture. The bay wall aperture is closeable, for example, by means of a rolling gate and, in practice, is to be opened only for the purpose of loading and unloading the refuse treatment space (16). Consequently, the aerobic degradation processes can proceed optimally in the refuse treatment space, and harmful emissions cannot pass out of the refuse treatment space (16) into the bay (5). Preferably, the aperture is closeable, airtight, with respect to the bay (5). In one embodiment, add-on walls (18) are provided, which laterally delimit the individual refuse treatment space (16). The add-on walls (18) are erected on the floor (50) and have a maximum height of 2.50 m to 3 m. The height of the add-on walls (18) is preferably 2 m to 2.50 m.

The refuse treatment spaces (16) each have a covering tarpaulin (30) which is provided with a raising and lowering device (20). In one version, the raising and lowering device (20) is formed by means of a pneumatic supporting structure (22) consisting, for example, of inflatable hoses (23).

The aerobic treatment process takes place in the refuse treatment space (16). For this purpose, the refuse treatment space (16b) is in a lowered state, that is to say the raising and lowering device (20) is lowered, so that the covering tarpaulin (30) fastened to it lies directly on the refuse to be treated. On the opposite bay wall (6), the refuse treatment space (16a) is illustrated in an erected state, that is to say the raising and lowering device (20) and the covering tarpaulin (30) fastened to it are raised. The raising operation results in the formation of a space which is accessible to loading and unloading appliances or loading and unloading vehicles. Refuse (2) can thus be transported into the space or transported out of the space through the bay wall aperture.

The covering tarpaulin (30) has a covering tarpaulin margin (32) which is arranged rigidly, and so as to be airtight, by means of a fastening device (40) against the bay wall (6) and on add-on walls (18) delimiting the refuse treatment space (16). In the event that add-on walls are absent, the covering tarpaulin margin (32) is directly anchored, airtight, on the floor (50).

FIG. 1A shows an enlarged illustration of the refuse treatment space (16a) from FIG. 1 in the raised state. The refuse treatment space (16a) is formed by a covering tarpaulin (30) which is provided with a raising and lowering device (20). In one embodiment, the raising and lowering device is a pneumatic height adjustment structure (22) and is formed by inflatable hoses (23). The hoses are supplied with air via a fan (24). The covering tarpaulin margin (32) is fastened to the outside (8) of the bay wall (6) and on the add-on walls (18) by means of the fastening device (40).

FIG. 1B shows an enlarged illustration of the refuse treatment space (16b) from FIG. 1 in the lowered state. The hoses (23) of the pneumatic raising and lowering device (22) are without air, so that the covering tarpaulin (30) lies directly on the refuse heap.

FIG. 2 shows a top view of the refuse treatment plant (1) of FIG. 1. The bay (5) has connected to it a bay fan (4) which suction-extracts the air contaminated with emissions out of the interior of the bay (5). In the bay roof (9), an air supply aperture (11) is formed, through which clean air can flow into the bay (5). The air supply aperture (11) may be provided at any desired point on the bay. The opening of the bay access (12) also ensures the supply of fresh air. A constant vacuum is generated in the bay (5), which means that the air pressure in the bay (5) is lower than atmospheric pressure. This prevents the situation where contaminated air may escape in an uncontrolled way into the surroundings. The bay fan (4) is connected to a waste-air filter (3), for example to a biofilter, which purifies the suction-extracted bay air. The bay fan (4) and the waste-air filter (4) together form a waste-gas purification device.

A plurality of refuse treatment spaces (16) are arranged in a rakelike or terminal formation in each case on the respective outside (8) of the lateral bay walls (6) lying opposite one another. Each refuse treatment space (16) has a raising and lowering device (20).

FIG. 3 shows a perspective view of an embodiment of the refuse treatment plant (1) according to the invention, with a bay (5) and in each case three coupled refuse treatment spaces (16) on the side walls (6) lying opposite one another. The bay (5) is constructed with at least one bay wall (6), with a bay roof (9) and with a bay access (12). A bay fan (4) is arranged on one end face of the bay (5) and sucks the waste air out of the bay. Depending on the size of the plant (1), even a plurality of fans and biofilters may be provided. In the bay roof (9), the air supply aperture (11) ensures fresh ambient air in the bay (5). In each case three refuse treatment spaces (16) are coupled to the outsides (8) of the lateral bay walls (6). Each refuse treatment space (16) is formed by a covering tarpaulin (30) with a covering tarpaulin margin (32). Moreover, each refuse treatment space (16) is delimited on the floor side by add-on walls (18). The add-on walls (18) serve as an outer lateral boundary of the refuse treatment space (16), and, at the same time, the transport of the refuse into and out of the refuse treatment space (16) is facilitated and the piling up of the refuse in layers to form a refuse heap between the add-on walls (18) is simplified. The front refuse treatment space (16a) is illustrated in the raised state, and the other refuse treatment spaces (16b) are illustrated in the lowered state.

In the embodiment illustrated, the covering tarpaulin margin (32) is fastened to the bay wall (6) and to the add-on walls (18) by means of a fastening device (40). The covering tarpaulin (30) is provided with a pneumatic raising and lowering device (22) in the form of inflatable hoses (23). A lock aperture (which cannot be seen) is provided in the bay wall (6) in each case between each refuse treatment space (16) and the bay (5) and connects the interior of the bay (5) to the interior of the refuse treatment space (16). The lock aperture is predominantly closed and is to be opened only when refuse (2) or treated refuse is transported into or out of the refuse treatment space (16).

Each refuse treatment space (16) can assume two states by virtue of the raising and lowering device (20) of the covering tarpaulin (30). For the aerobic treatment process, the refuse treatment space (16b) is in a lowered state, which means that the covering tarpaulin (30) lies directly on the refuse. The refuse treatment space (16a) is in a raised state solely for filling and emptying the latter. The raising and lowering device (20) raises itself and consequently the covering tarpaulin (30) connected to the device. Loading and unloading appliances or vehicles can thus enter the interior of the refuse treatment space (16a).

The treatment space (16a) is in the raised state, that is to say the hoses (23) are inflated and have raised the covering tarpaulin (30). The refuse can be transported into or out of the refuse treatment space (16a) through the open bay wall aperture.

The refuse treatment spaces (16b) are in the lowered state. The hoses (23) are without air, and consequently the covering tarpaulin (30) lies on the refuse (2) and the aerobic degradation process can take place. The bay wall aperture is closed.

The covering tarpaulin margin (32) is the outer marginal boundary of the covering tarpaulin (30). The refuse treatment space (16) is firmly connected to the bay (5) and to the floor (50) or the add-on walls (18) via the covering tarpaulin margin (32). For this purpose, the covering tarpaulin margin (32) is arranged rigidly, and so as to be airtight, with respect to the bay wall (6) and to the floor or to the add-on walls by means of a fastening device (40). A refuse treatment space (16) closed with respect to the surroundings is consequently provided. The airtight fastening of the covering tarpaulin margin (32) has the effect that no unwanted airstreams of waste air can pass out of the inside of the refuse treatment space (16) into the surroundings, for example via air bridges between the covering tarpaulin margin (32) and the bay wall (6). The rigid fastening constitutes an immovable fastening in that, even during the operations of raising and lowering the covering tarpaulin (30), the covering tarpaulin margin (32) always remains firmly and immovably in its fastened position, so that the refuse treatment space (16) is always a closed system.

The refuse treatment space (16) has a front region, and end region and side regions lying between these. The front region adjoins the bay wall (6) and surrounds the bay wall aperture. The covering tarpaulin margin (32) in the front region is fastened to the bay wall (6). The covering tarpaulin margin (32) of the side regions and in the end region is fastened on or to the add-on walls (18). In a further embodiment, the covering tarpaulin margin (32) of the side regions and in the end region is fastened directly on the floor (50). The raising and lowering device (20) comprises a pneumatic supporting structure (22) or a mechanical height adjustment structure (26).

The pneumatic supporting structure (22) has a number of supporting elements (23) capable of being filled with at least one fluid and connected at least partially to one another. The fluid filling the supporting elements may be a gas, a vapor, a liquid or a gas and a liquid. This means that the supporting elements may be filled either with at least one gas or with at least one liquid or with at least one gas and at least one liquid. The supporting elements are designed so as to be at least gastight. The supporting elements are preferably inflated hoses (23).

In the embodiment shown in FIG. 3, the raising and lowering device (20) forms a semicircular tunnel with a front region and with an end region, the front region being fastened to the bay wall (6) via the covering tarpaulin margin (32). Depending on the configuration of the supporting elements, the device may assume any desired form in the erected state, such as, for example, parallelepipedal, dome-shaped, conical or pyramidal configurations.

The pneumatic raising and lowering device (22) may have any desired number of supporting elements. At least two supporting elements are required, however, in order to permit a sufficient fastening of the covering tarpaulin (30) and in order to give the entire device the necessary stability. In FIG. 3, there are preferably vertically and horizontally arranged supporting elements which are arranged crosswise with respect to one another. The supporting elements may also run obliquely at a specific angle with respect to the ground.

Each pneumatic raising and lowering device (22) has at least one fluid inlet (51) and at least one fluid outlet (53). In one embodiment the fluid inlet (51) is at the same time also the fluid outlet (53). Each supporting element may have a specific fluid inlet (51) and fluid outlet (53) or, if the supporting elements are connected to one another such that the fluid can flow through all the supporting elements, one fluid inlet (51) and one fluid outlet (53) are sufficient for all the supporting elements. The fluid inlet (51) is an aperture in a supporting element, a connection piece to the fan (24) being welded into or onto said aperture. The connection piece may, for example, be a PVC tube. The fluid outlet (52) is a commercially available valve, for example from the company Scoprega S.p.A., Milan, Italy. A fan (24) is connected, outside the pneumatic raising and lowering device (23), to the fluid inlet (51) and supplies the supporting elements with at least one fluid.

The supporting elements (23) are connected at least partially to one another, which covers all the embodiments in which the supporting elements (23) are connected directly to one another at their contact points, the supporting elements (23) are connected to one another only at individual contact points, only individual supporting elements are connected to one another or the supporting elements (23) are connected indirectly to one another via aids, such as, for example, connecting battens, connecting rails or connecting cords. The supporting elements (23) may, for example, be connected to one another solely via the covering tarpaulin. Preferably, each supporting element (23) is connected to an adjacent supporting element (23) at individual contact points. The connection of the supporting elements (23) has the effect that a stable and self-supporting structure is obtained in the erected state. In one embodiment, the supporting elements (23) lie one above the other at their crossing points or contact points and are connected with one another in such a way that those surfaces of the horizontal and vertical supporting elements (23) which touch one another are adhesively bonded, stitched or welded to one another or connected to one another in another way.

In another embodiment, the supporting elements (23) are connected to one another at the crossing points or contact points such that the cross sections of the horizontal supporting elements project into the cross sections of the vertical supporting elements. The at least one fluid can consequently flow from one point through the entire structure of the supporting elements (23). This is particularly advantageous because only one fan (24) needs to be connected to the raising and lowering device. Moreover, this structure is particularly stable since an advantageous pressure distribution is established.

In a further embodiment, only individual vertically erected supporting elements are provided which are connected to one another via a horizontal fluid pipe. The fluid pipe may run in the roof gable or near the ground and distributes the fluid flowing in via the fluid inlet (51) to all the supporting elements. The fluid pipe is preferably a rigid plastic or metal pipe which must withstand the pressure prevailing at the fluid inlet (51). It may, however, also be manufactured from flexible gastight materials.

Finally, the supporting elements (23) may be arranged in any desired arrangement with respect to one another insofar as a three-dimensional structure is consequently provided in the erected state.

The supporting elements (23) can be filled with at least one fluid, such as liquids or gases, that is to say it must have a cross section through which gases or liquids are capable of flowing. Possible reinforcing elements inside the supporting elements (23) should not appreciably impede their throughflow capacity. The cross section of the supporting elements (23) should have a diameter of at least 10 cm for a sufficient stability and bearing surface for the covering tarpaulin (30). The diameter preferably amounts to 50 cm. In a further preferred embodiment, the supporting elements have a diameter of at least 80 cm, and preferably the diameter lies between 90 cm and 110 cm.

The supporting elements may be any desired three-dimensional structures, such as, for example, hoses or other hollow bodies. In a preferred embodiment, the supporting elements (23) are hoses. The supporting elements (23) may have any desired cross-sectional form, a round cross section being particularly preferred. A round cross section is simple to produce and allows an optimal pressure distribution within the supporting elements (23). The supporting elements may, for example, also have an oval cross section.

In one embodiment, the supporting elements are hoses (23) inflatable with gas. The gas used is preferably air which has an excess pressure of at least 200 Pa in the supporting elements (23). The air preferably has an excess pressure of at least 10 kPa. In one embodiment, work is carried out with an excess pressure of between 15 and 22 kPa. In addition to air, helium or other available gases may also be employed.

In a further embodiment, the supporting elements (23) can be filled with a liquid, such as, for example, water.

The supporting elements (23) may also be filled with a liquid and a gas, in which case, preferably, the liquid is introduced in a lower part of the supporting elements (23) and the gas is introduced into an upper part of the supporting elements (23). In this case, the lower part comprises the near-ground region of the supporting elements (23), such as, for example, the wall region, and the upper part comprises a ground-distant region, such as, for example, the roof region. The advantage of this is that the liquid at the same time stabilizes the device on the ground (50).

In order to prevent too high a pressure in the supporting elements, at least one pressure relief valve (55) is provided. This at least one pressure relief valve (55) opens, for example, at an internal pressure of more than 25 kPa and thus prevents a possible destruction of the supporting elements due to excess pressure. For example, a pressure relief valve from the manufacturer Halkey Roberts, St Petersburg, Fla., USA, may be employed.

A watertight and airtight material, such as, for example, a PVC-coated carrier fabric serves as material for the supporting elements (23). The material should be sufficiently weather-resistant and hard-wearing, in order to allow a long lifetime. Preferably, the material is flexible and consequently foldable or drapable, so that, in the lowered state, the supporting elements (23) can collapse on themselves. The feature of drapability is important for the present invention, so that, during and after the emptying of the supporting elements (23), the collapse of the device can be controlled, so as to achieve an exact placing of the covering tarpaulin (30) on the surface of the refuse heap.

The covering tarpaulin (30) of the refuse treatment space (16) is arranged either on the top side or on the underside of the supporting elements (23) of a pneumatic raising and lowering device (20).

In a further embodiment, the covering tarpaulin (30) is arranged between the supporting elements (23), specifically such that the surfaces delimited in the circumferential direction by the supporting elements (23) are filled by the covering tarpaulin (30).

Preferably, the covering tarpaulin (30) is located on the underside of the supporting elements. The covering tarpaulin (30) will be fastened to the supporting elements (23) by means of any known type of fastening, this including fastening possibilities, such as binding, stitching, adhesive bonding, welding, with press studs or magnetic buttons, with touch-and-close fastenings, with hooks or with a zip fastening. Preferably, the covering tarpaulin (30) is fastened releasably to the supporting elements (23), in order to make it possible to change the covering tarpaulin (30) easily and quickly if the latter is soiled or damaged.

In one embodiment, the covering tarpaulin (30) covers the entire underside of the supporting elements (23).

In another embodiment, the covering tarpaulin (30) covers only the underside of the roof region of the raising and lowering device (20). This particularly cost-effective version uses additionally a watertight protective layer (56) which is applied in the wall region of the raising and lowering device (20). This watertight protective layer (56), as a rule, is more cost-effective than the covering tarpaulin (30) and has a robust abrasion-resistant material, such as, for example, a PVC-coated carrier fabric. Additional protection of the refuse treatment space (16) against damage to the side walls in the raised state by machines and vehicles is consequently achieved.

For a sufficient aeration of the refuse heap in the refuse treatment space, the covering tarpaulin (30) must have sufficient air-permeability to ensure the aerobic degradation processes of the organic constituents in the refuse. The air-permeability of the covering tarpaulin (30) preferably lies between 3 and 100 $m^3/m^2/h$ in the case of an applied pressure difference of 200 Pa.

The covering tarpaulin (30) is liquid-tight at a water inlet pressure higher than 10 kPa, preferably higher than 50 kPa, the water inlet pressure possibly amounting to 1 MPa.

The water vapor flow resistance Ret of the covering tarpaulin (30) amounts to less than 15 $m^2$ Pa/W, preferably less than 10 $m^2$ Pa/W.

The covering tarpaulin is a gas-permeable and watertight textile, a gas-permeable and watertight membrane or a laminate with a gas-permeable and watertight membrane. The textile used may be a tightly pressed or tightly woven textile, such as, for example, a high-strength polyester fabric.

The covering tarpaulin (30) must be made from a flexible and therefore foldable and drapable material, so that, in the lowered state of the raising and lowering device (20), it can be placed onto the surface of the refuse heap and excess material of the covering tarpaulin and of the supporting elements can be folded around the refuse heap.

Preferably, the liquid-tight and gas-permeable covering tarpaulin used is a laminate with a membrane (34) with at least one textile layer (36). Preferably, the membrane (34) is porous, and the pores of the membrane must be sufficiently large to allow the necessary gas throughput. The membrane (34) is, for example, a material from the group of polyolefins, polyesters, polyvinylchlorides, polyvinylidenechlorides, polyurethanes or fluoropolymers. Preferably, the porous membrane is a microporous membrane. Membranes are thin, light, flexible and drapable. In addition, they are permeable to water vapor, air-permeable and watertight.

Preferred microporous membranes contain fluoropolymers, such as, for example, polytetrafluoroethylene; polyolefins, such as polyethylene or polypropylene; polyamides, polyesters; polysulfones, polyethersulfones and combinations thereof; polycarbonates; polyurethanes. Preferably, a membrane consisting of oriented polytetrafluoroethylene (ePTFE) is used. The membrane consisting of ePTFE has a thickness of between 5 and 500 µm, preferably of between 15 and 60 µm.

This material is distinguished by a multiplicity of open interconnected voids, a large void volume and high strength. Expanded polytetrafluoroethylene (ePTFE) is soft, flexible, has stable chemical properties, high permeability with respect to gases and vapors and a surface with good repulsion against impurities. On account of its high cold buckling resistance, it is suitable for use in all climatic zones.

Furthermore, this material is permeable to gas. Porosity and pore size are selected such that gas diffusion is not impeded. The average pore size may amount to 0.1-100 µm, preferably 0.2-10 µm, determined according to the Coulter test described above. Porosity amounts to 30-90%, preferably 50-80%. The material is at the same time watertight. A method for the production of such porous membranes from oriented PTFE is disclosed, for example, in the patents U.S. Pat. No. 3,953,566 and U.S. Pat. No. 4,187,390.

Preferably, the microporous membrane is provided with a textile carrier material which gives the membrane additional protection and strength. The carrier material may be laminated on at least one of the surfaces of the membrane by means of a continuous or discontinuous adhesive layer. Advantageously, the carrier material is a sheetlike textile structure consisting of woven, knitted, natural or synthetic textile materials. Contextures and nonwovens may also be used. Suitable textile materials are, in particular, polyesters, polyamides, polyethylene, polyacrylates, polypropylene, glass fiber, fluoropolymers or a textile woven from PTFE. There is provision for the carrier material to be arranged outwardly toward the atmosphere. Alternatively, a further sheetlike textile structure may be arranged on the other membrane surface.

In a further embodiment, the membrane is made oil-repellant. Oil-repellant treatment of the membrane takes place in such a way that the porosity of the membrane is not markedly reduced. Preferably, the membrane has an oil rate of >1, ideally the oil rate is >5, so that moistening and contamination with organic substances are permanently avoided. Oil-repellant treatment is described, for example, in DE 43083692. An oil-repellant ePTFE membrane is particularly preferred for the present invention. The oil-repellant microporous membrane may have at least one textile carrier layer laminated on.

Where the textile carrier materials are concerned, comparably high oil rates are achieved, using commercially available fluorocarbon coatings. An oil-repellant agent is usually applied in liquid form to the material to be made oil-repellant, such as, for example, by immersion, impregnation, spraying, coating, brushing or rolling.

Figure 4:
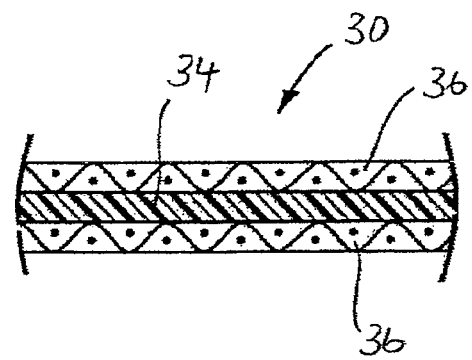
FIG. 4 shows a cross section through the covering tarpaulin of a refuse treatment space.

A particularly preferred covering tarpaulin in the form of a 3-ply laminate is illustrated in FIG. 4. A watertight membrane (34) permeable to water vapor is arranged between two textile carrier materials (36). The membrane is a microporous membrane consisting preferably of ePTFE. The pore size of the membrane is 0.1 to 100 µm, preferably 0.2 to 10 µm. Such a small pore size prevents the situation where germs and bioaerosols may penetrate outward. A sufficient gas exchange with the surroundings is ensured at the same time.

Such a laminate is described, for example, in WO 01/21394 A1 and is obtainable from the company W.L Gore & Associates GmbH, Putzbrunn near Munich, under the name Gore®-Cover.

Figure 5:
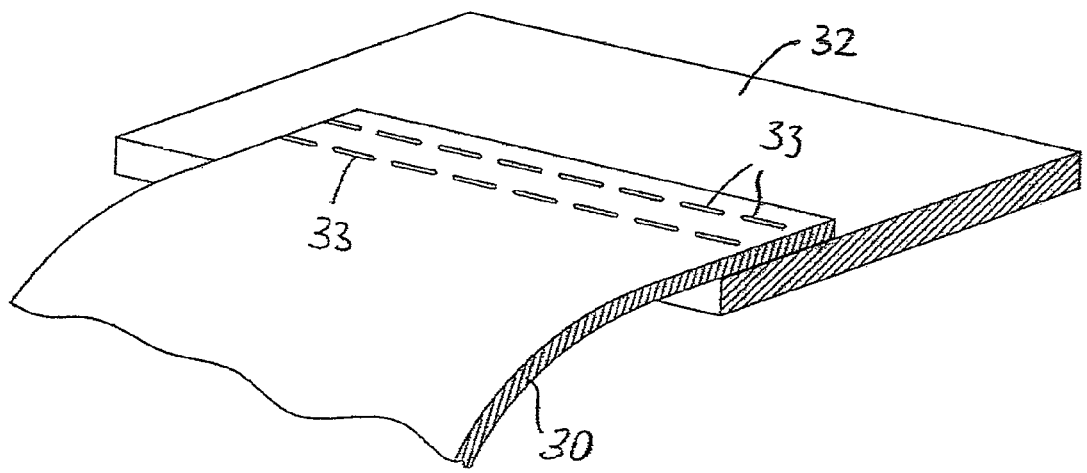
FIG. 5 shows an embodiment of the covering tarpaulin margin.

FIG. 5 shows an embodiment of the covering tarpaulin margin (32). For this, a large-area reinforcing strip is fastened to the outer margin of the covering tarpaulin (30). This reinforcing strip forms the covering tarpaulin margin (32) and is formed, for example, by a large-area strip by means of polyester fabrics coated on both sides with PVC. On account of its robust material structure, the reinforcing strip is highly resistant to the fastening device. This strip is fastened along the outer margin of the covering tarpaulin (30), for example by means of a plurality of seams (33), in order, inter alia, to prevent the situation where the reinforcing strip is torn from the covering tarpaulin (30) as a result of stress occurring during the raising and lowering operations. Instead of seams, methods, such as adhesive bonding or welding, may also be employed in order to attach the strip.

Figure 6:
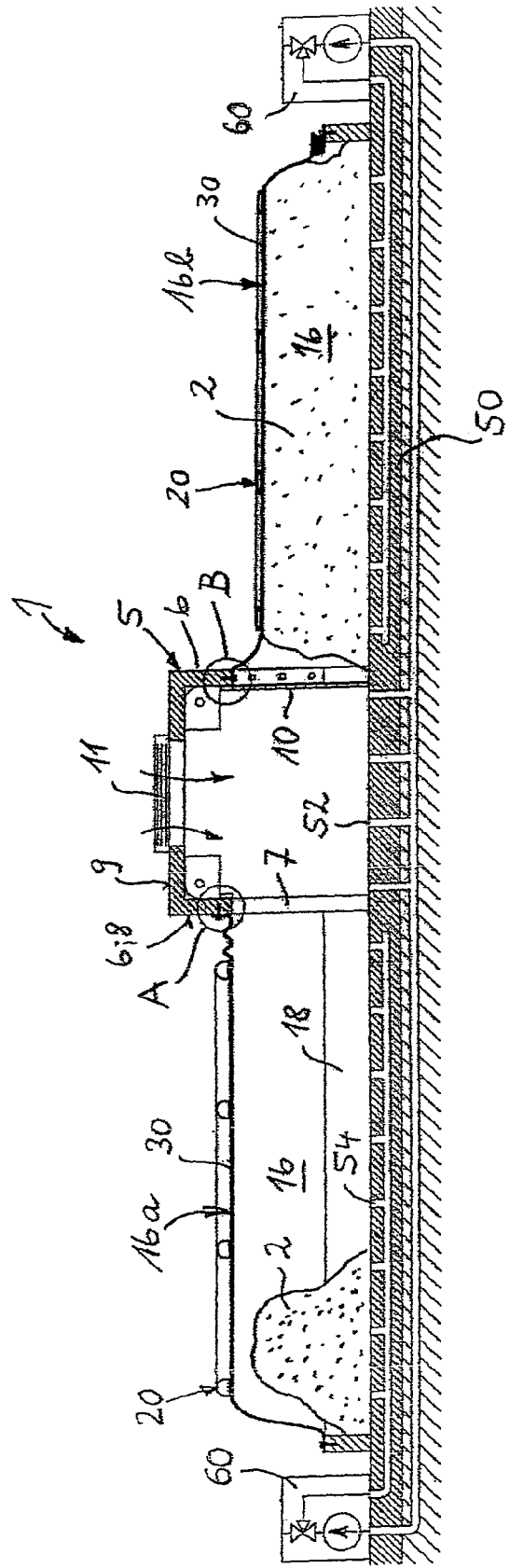
FIG. 6 shows a diagrammatic sectional illustration through the refuse treatment plant in FIG. 1.

FIG. 6 shows a section along the sectional line VI-VI through the refuse treatment plant (1) according to FIG. 3. The bay (5) lies between the refuse treatment spaces (16a) and (16b). An air aperture (11) for the supply of fresh air into the interior of the bay (5) is located in the roof of the bay. The refuse treatment spaces (16a) and (16b) are connected in each case to the bay (5) via a closeable bay wall aperture (7). The bay wall aperture (7) is closeable, for example, by means of a door (10) in the form of a rolling gate. The refuse treatment space (16a) is illustrated in the raised state. The covering tarpaulin (30) is raised by means of the raising and lowering device (20) and is located at a distance above the refuse heap (2). The bay wall aperture (7) is opened, so that, for example, wheeled loaders can drive in in order to build up or break down the refuse heap. The refuse treatment space (16b) is in the lowered state, and therefore the raising and lowering device (20) is lowered and the covering tarpaulin (30) directly covers the refuse heap. The bay wall aperture (7) is closed.

The respective covering tarpaulin margin (32) of each treatment space (16a, 16b) is fastened to the bay wall (6) and to the add-on walls (18) by means of a fastening device (40). The fastening device (40) serves for arranging the covering tarpaulin margin (32) rigidly, and so as to be airtight, with respect to the bay wall (6) and to the floor (50). The fastening device (40) comprises fixing elements, such as, for example, screws, nails, pins, clamps or rivets, which are anchored over a large area, and so as to be airtight, through the covering tarpaulin margin (32) in the bay wall (6) or the add-on walls (18) or the floor (50). The covering tarpaulin margin (32) thus remains rigidly and immovably in its fastened position even during the raising and lowering operations, and the entire refuse treatment space (16) thus remains closed with respect to the surroundings. Moreover, the arrangement of the covering tarpaulin margin (32) by means of the fastening device (40) is airtight, that is to say no unwanted air and consequently no harmful emissions can escape from the interior of the refuse treatment space (16).

The entire refuse treatment space is thus particle-tight, which means that no particles >0.3 μm can leave the refuse treatment space either through the covering tarpaulin or through the connection between the covering tarpaulin and bay wall or add-on walls. Only when the bay wall aperture (7) is being opened can harmful emissions escape into the bay interior, but these are suction-extracted there and supplied for waste air treatment.

Owing to unevennesses in the surface of the walls and of the floor and also because of creasing of the covering tarpaulin margin (32) when it is being arranged on the walls and the floor, it may be necessary to arrange at least one sealing ply (42) consisting of an adaptable material between the covering tarpaulin margin (32) and wall or floor. The sealing ply serves for compensating the unevennesses in the walls or floor and for eliminating them, in order to bring about an airtight fastening of the refuse treatment space (16) to the bay. An airtight form fit between the walls (6, 18) and the covering tarpaulin margin (32) is to be formed with the aid of the sealing ply or of the adaptable material (42). This prevents the situation where air bridges are formed within the fastening of the covering tarpaulin margin (32) and unwanted air can pass out of the interior of the refuse treatment space into the surroundings. In one embodiment, the adaptable material is an elastic and soft material, such as, for example, a rubber or foam. The adaptable material selected may be a flexible material from the material group containing foam, rubber, coated carrier substances, polymer strips or coated textiles. Embodiments of the fastening device (40) are illustrated in FIGS. 7 to 9.

In a further embodiment, a number of first floor apertures (52) are provided in the floor of the bay (5). In addition to the bay deaerator (4), air can be discharged from the bay (5) through first floor apertures (52).

A number of second floor apertures (54) are provided in the floor of the interior of the refuse treatment space (16a, 16b). These serve for conducting air into the refuse treatment space via separate fans (60), so that the refuse heap is aerated.

In a further embodiment, the waste air is sucked out of the bay (5) via the first floor apertures (52) and is supplied to the second floor apertures (54) via floor ducts. Basically, each individual refuse treatment space is assigned individual fans (60) which conduct air or, if required, waste air into the interior of the refuse treatment space (16) during the aerobic treatment process. The suction-extracted bay air can thus be used for aerating the refuse. This air then passes through the gas-permeable membrane (34) of the covering tarpaulin (30) into the surroundings again. A purification of the air then takes place in the pore structure of the membrane.

Figure 6A:
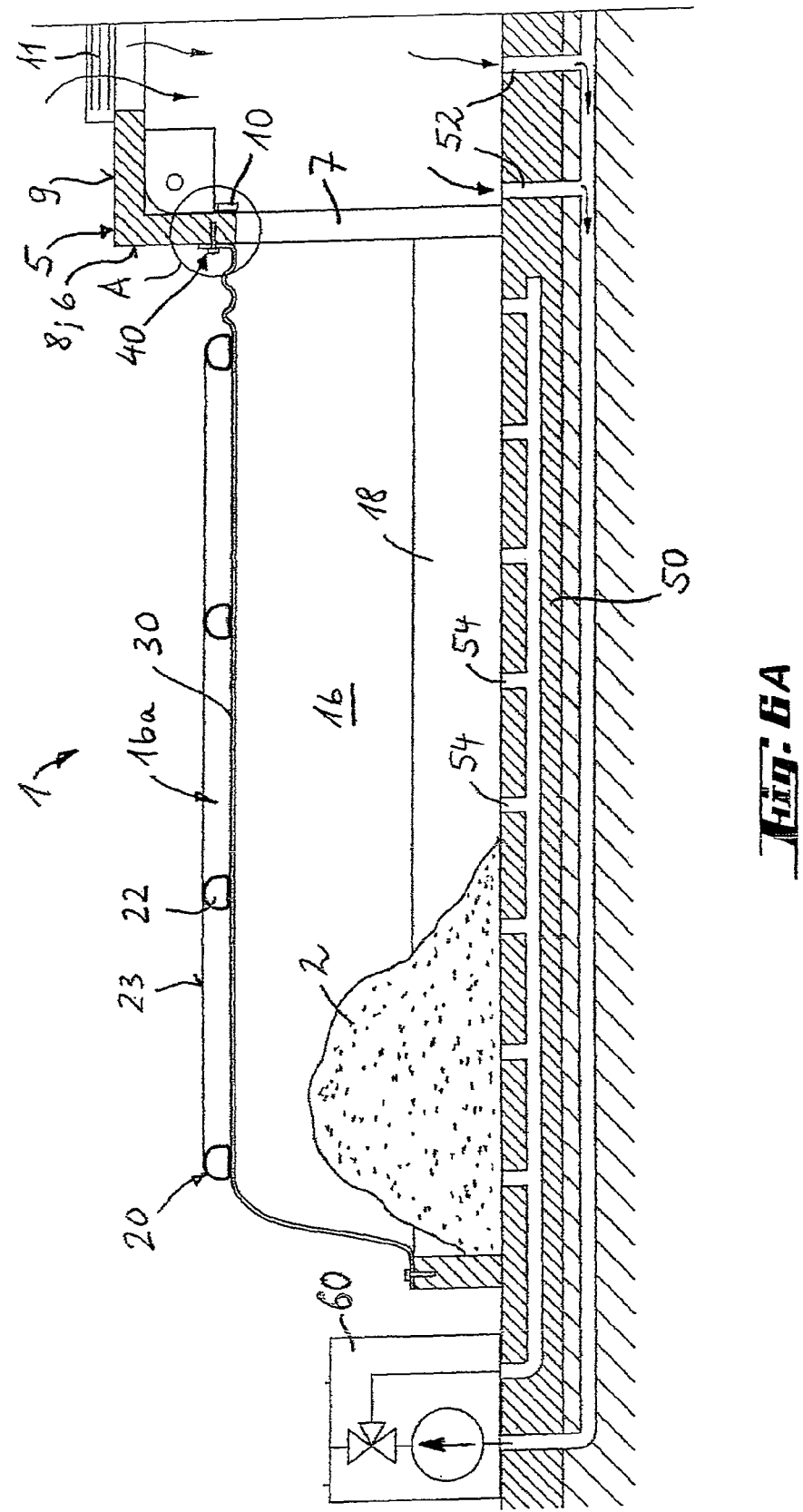
FIG. 6A shows a diagrammatic enlargement of the refuse treatment space 16a from FIG. 6.

FIG. 6A shows an enlarged illustration of the refuse treatment space (16a) from FIG. 6 in the raised state. The pneumatic raising and lowering device (22) is filled with air, and the bay wall aperture (7) is opened for the purpose of filling or emptying the refuse treatment space (16a). Second floor apertures (54) serve for the supply of aerating air. The contaminated air from the bay (5) is suction-extracted out of the interior of the bay (5) by means of the bay fan (4) via the first floor apertures (52) and is discharged into the surroundings after being purified in a waste air filter (3).

FIG. 6B shows an enlarged illustration of the refuse treatment space (16b) from FIG. 6 in the lowered state. The hoses (23) of the pneumatic raising and lowering device (22) are without air, and the covering tarpaulin (30) therefore lies directly on the refuse (2). The bay wall aperture (7) is closed by means of a door (10). The suction-extracted waste air from inside the bay (5) is conducted as aerating air into the refuse treatment space (16b) via the second floor apertures (54).

FIG. 7 shows an enlarged illustration of an embodiment of the fastening device (40) in the region A in FIG. 6. A sealing ply consisting of an adaptable material (42) is arranged between the bay wall (6) and the covering tarpaulin margin (32). This material serves for compensating unevennesses in the bay wall (6), so that no air ducts are formed between the covering tarpaulin margin (32) and the bay wall (6). In one embodiment, the sealing ply is a permanently deformable PVC film and is in the form of a sheetlike strip with a width of, for example, 10 cm. The covering tarpaulin margin (32) has arranged on it a plate (46) which is screwed together with the other plies to the bay wall (6), in order to ensure a large-area pressure force on the covering tarpaulin margin (32) and the sealing ply (42). This plate (46) may be a metal plate with regularly arranged orifices for the fastening screws (44). The screws (44) are fixed through the plate (46), the covering tarpaulin margin (32) and the sealing ply (42) in the bay wall (32). By the screws being tightened, the metal plate presses over a large area onto the covering tarpaulin margin (32) and the sealing ply (42) and presses the plies rigidly against the bay wall (6). An airtight form fit arises between the bay wall (6) and the covering tarpaulin margin (32). In the region of the add-on walls (18), the covering tarpaulin margin (32) is fastened rigidly, and so as to be airtight, on or to the respective add-on wall according to the same fastening set-up described above. This applies to a fastening on the floor (50).

FIG. 8 shows an enlarged illustration of a further embodiment of the fastening device (40) in the region A in FIG. 6. Here, the covering tarpaulin margin (32) is formed by a reinforcing strip according to FIG. 5. The reinforcing strip has sufficient strength so that the plate (46) may be dispensed with. The screws (44) thus fix the reinforcing strip (32) and the sealing ply (42) to the bay wall (6) in an airtight manner.

FIG. 9 shows an enlarged illustration of a further embodiment of the fastening device (40) in the region B in FIG. 6. The arrangement corresponds as far as possible to FIG. 7, although the plies are fastened angularly to the bay wall aperture (7) and to the inside of the bay wall (6).

FIG. 10 shows a further embodiment of the fastening device (40). The covering tarpaulin margin (32) is clamped, airtight, in a frame (48) correspondingly to the form of the bay wall aperture (7). The frame (48) is fitted, airtight, into the bay wall aperture (7). This embodiment brings about a particularly simple type of fastening of the covering tarpaulin (30) to the bay wall (6). The remaining covering tarpaulin margin may be fastened to the floor (50) or on or to the add-on walls by means of a horizontally formed clamping frame (49).

Figure 11:
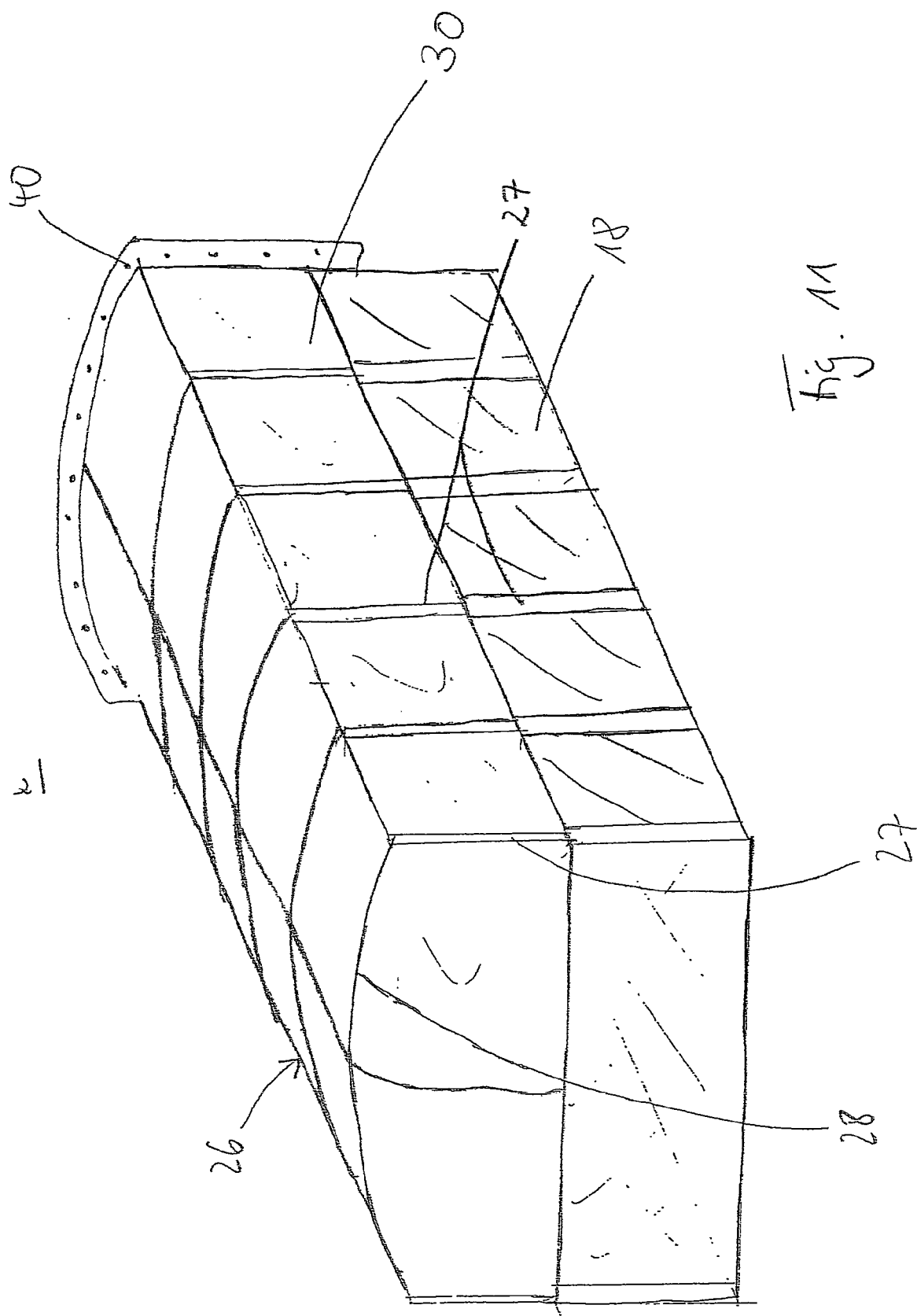

FIGS. 11 and 12 show a refuse treatment plant (1) with a treatment space (16) which has a raising and lowering device (20) in the form of a mechanical height adjustment structure (26). Preferably, this structure (26) consists of metals, in particular high-grade steel. For this purpose, telescopically extendable carriers (27) are fastened to the add-on walls (18). The carriers (27) are connected to supporting bars (28) to form a stand of adjustable height. The covering tarpaulin (30), which forms the refuse treatment space (16), is fastened to the inside or outside of the stand. In FIG. 11, the carriers (27) are extended, and the covering tarpaulin (30) is raised and is located at a distance above the refuse heap. The covering tarpaulin margin (32) is fastened rigidly, and so as to be airtight, to the bay wall (6) and the add-on walls (18) by means of the fastening device (40) described above. In FIG.

12, the carriers (27) are pushed one into the other, and the refuse treatment space (16) is in a lowered state, so that the covering tarpaulin (30) lies on the refuse heap and accelerates the aerobic treatment process.

The invention claimed is:
1. A refuse treatment plant (1), with
   a) a bay (5) with at least one bay wall (6), with a bay roof (9) and with an access (12) for the introduction and removal of refuse (2),
   b) with an aeration and deaeration plant (14) for the supply and discharge of air into and out of the bay (5),
   c) with at least one refuse treatment space (16) arranged on an outside of the bay wall (6), and
   d) with a bay wall aperture (7), connecting the bay (5) to the refuse treatment space (16), for introducing the refuse (2) from the bay (5) into the refuse treatment space (16) and for removing the treated refuse from the refuse treatment space (16) into the bay (5),
   e) the refuse treatment space (16) is formed by a covering tarpaulin (30) provided with a raising and lowering device (20) and having a covering tarpaulin margin (32), the covering tarpaulin margin (32) being arranged rigidly, and so as to be airtight, with respect to the bay wall (6) and to the floor by means of a fastening device (40).
2. The plant (1) as claimed in claim 1, the refuse treatment space (16) having add-on walls (18) which delimit the refuse treatment space (16) on the floor side, and the covering tarpaulin margin (32) being arranged rigidly, and so as to be airtight, with respect to the bay wall (6) and to the add-on walls (18).
3. The plant (1) as claimed in claim 1, the fastening device (40) having at least one adaptable material (42).
4. The plant (1) as claimed in claim 3, the material (42) being selected from the material group containing flexible materials, such as foam, rubber, coated carrier substances and polymer strips.
5. The plant (1) as claimed in claim 3, the material (42) having a coated textile.
6. The plant (1) as claimed in claim 3, the material (42) being arranged in each case between the covering tarpaulin margin (32) and the bay wall (6) and between the covering tarpaulin margin (32) and the floor (50).
7. The plant (1) as claimed in claim 2, the material (42) being arranged in each case between the covering tarpaulin margin (32) and the bay wall (6) and between the covering tarpaulin margin (32) and the add-on walls (18).
8. The plant (1) as claimed in claim 1, the fastening device (40) having at least one clamping frame (48) into which the covering tarpaulin margin (32) is clamped.
9. The plant (1) as claimed in claim 1, the fastening device (40) comprising fixing elements, such as screws, nails, clamps or rivets.
10. The plant (1) as claimed in claim 1, the refuse treatment space (16) being particle-tight with respect to the surroundings.
11. The plant (1) as claimed in claim 1, the covering tarpaulin (30) having a watertight and gas-permeable membrane (34).
12. The plant (1) as claimed in claim 11, the membrane (34) being porous.
13. The plant (1) as claimed in claim 11, the membrane (34) being selected from the group of polyolefins, polyesters, polyvinylchlorides, polyurethanes or fluoropolymers.
14. The plant (1) as claimed in claim 11, the membrane (34) having oriented polytetrafluoroethylene (ePTFE).
15. The plant (1) as claimed in claim 11, the membrane (34) being connected to at least one textile layer (36).
16. The plant (1) as claimed in claim 15, the textile layer (36) having polyester, polyamide, polyethylene, polyacrylate, polypropylene, glass fiber or fluoropolymer.
17. The plant (1) as claimed in claim 11, the covering tarpaulin (30) having an air-permeability of between 3 and 100 $m^3/m^2/h$ in the case of a pressure difference of 200 Pa.
18. The plant (1) as claimed in claim 1, the raising and lowering device (20) comprising a pneumatic supporting structure (22) or a mechanical height adjustment structure (26).
19. The plant (1) as claimed in claim 18, the pneumatic supporting structure (22) providing a number of inflatable hoses (23).
20. The plant (1) as claimed in claim 19, the hoses (23) withstanding a pressure of at least 10 kPa.
21. The plant (1) as claimed in claim 18, the pneumatic supporting structure (22) providing a number of hoses capable of being filled with liquid.
22. The plant (1) as claimed in claim 18, the mechanical height adjustment structure (26) having carriers (27) of adjustable height.
23. The plant (1) as claimed in claim 22, the carriers (27) being telescopically extendable.
24. The plant (1) as claimed in claim 1, a number of first floor apertures (52) being provided in the floor of the bay (5), and the aeration and deaeration plant (14) discharging air out of the interior of the bay (5) via the floor apertures (52).
25. The plant (1) as claimed in claim 1, a number of second floor apertures (54) being provided in the floor of the interior of the refuse treatment space (16), and the aeration and deaeration plant (14) supplying the discharged air from the bay (5) to the interior of the refuse treatment space (16) via the second floor apertures (54).
26. The plant (1) as claimed in claim 1, the bay wall aperture (7) being closeable.
27. The plant (1) as claimed in claim 1, the aeration and deaeration plant (14) having at least one waste air filter (3).

* * * * *